US012599472B2

(12) United States Patent (10) Patent No.: US 12,599,472 B2
Xiao et al. (45) Date of Patent: Apr. 14, 2026

(54) COVERED STENT

(71) Applicant: LIFETECH SCIENTIFIC (SCIENTIFIC) CO., LTD., Shenzhen (CN)

(72) Inventors: Benhao Xiao, Shenzhen (CN); Caiping Liu, Shenzhen (CN)

(73) Assignee: LIFETECH SCIENTIFIC (SCIENTIFIC) CO., LTD., Shenzhen (CN)

( * ) Notice: Subject to any disclaimer, the term of this patent is extended or adjusted under 35 U.S.C. 154(b) by 134 days.

(21) Appl. No.: 18/386,216

(22) Filed: Nov. 1, 2023

(65) Prior Publication Data

US 2024/0065823 A1 Feb. 29, 2024

Related U.S. Application Data

(63) Continuation of application No. 17/617,885, filed on Dec. 9, 2021, now Pat. No. 11,806,225.

(51) Int. Cl.
*A61F 2/07* (2013.01)
*A61F 2/06* (2013.01)

(52) U.S. Cl.
CPC .......... *A61F 2/07* (2013.01); *A61F 2002/061* (2013.01); *A61F 2230/0091* (2013.01); *A61F 2250/0098* (2013.01)

(58) Field of Classification Search
CPC .................. A61F 2/07; A61F 2002/061; A61F 2230/0091; A61F 2250/0098; A61F 2230/0008
See application file for complete search history.

(56) References Cited

U.S. PATENT DOCUMENTS

| | | | | | |
|---|---|---|---|---|---|
| 2005/0102021 | A1* | 5/2005 | Osborne | .................... | A61F 2/07 |
| | | | | | 623/1.13 |
| 2011/0313504 | A1* | 12/2011 | Golding | .................... | A61F 2/07 |
| | | | | | 623/1.11 |
| 2012/0035714 | A1* | 2/2012 | Ducke | ....................... | A61F 2/07 |
| | | | | | 623/1.34 |
| 2015/0216686 | A1* | 8/2015 | Chakfe | ..................... | A61F 2/07 |
| | | | | | 623/1.35 |

* cited by examiner

*Primary Examiner* — Sarah W Aleman
*Assistant Examiner* — Rebecca Lynee Zimmerman
(74) *Attorney, Agent, or Firm* — Raymond Sun

(57) ABSTRACT

Disclosed is a covered stent (100), including a hollow tubular main body (10), and a window (20) provided on a side wall of the tubular main body (10). An elastic supporting member (30) is provided at a periphery of the window (20); an imaging member (40) is provided on the elastic supporting member (30); and at least part of the imaging member (40) is movably connected to the elastic supporting member (30). Since the imaging member (40) and the elastic supporting member (30) are located at the periphery of the window (20), the imaging member (40) and the elastic supporting member (30) enable the periphery of the window (20) to simultaneously have a good imaging performance and a good supporting performance.

9 Claims, 7 Drawing Sheets

30

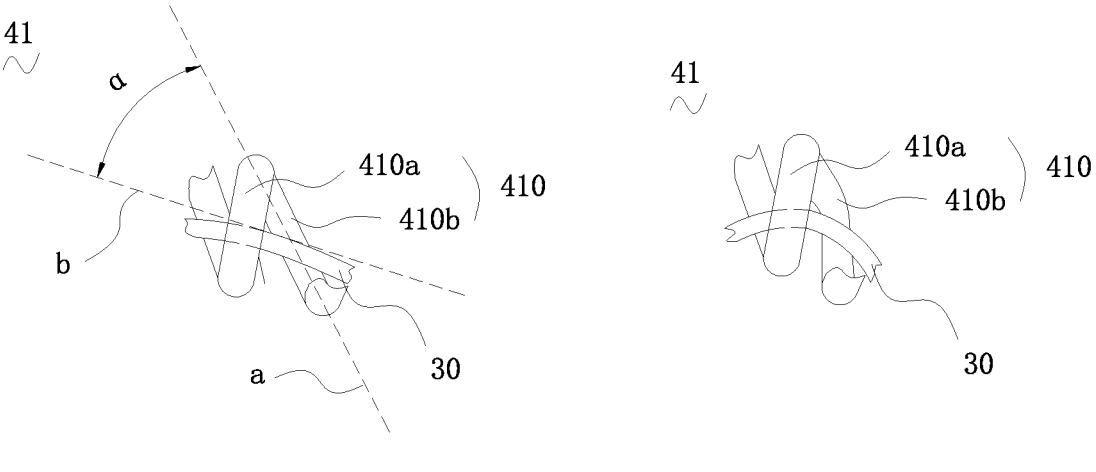
FIG. 5a                    FIG. 5b
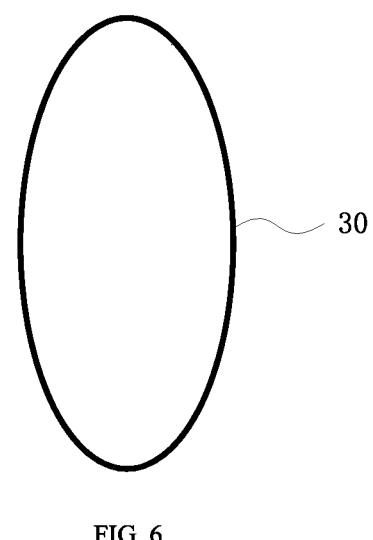
FIG. 6

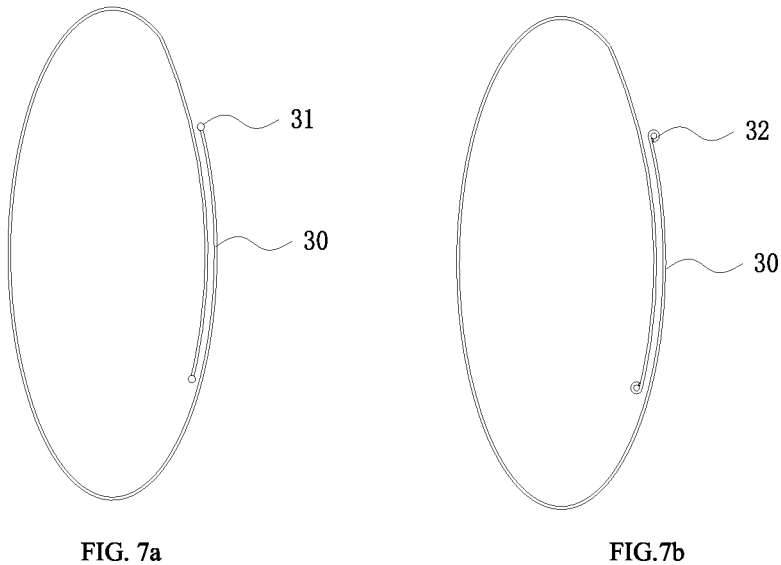
FIG. 7a                    FIG.7b
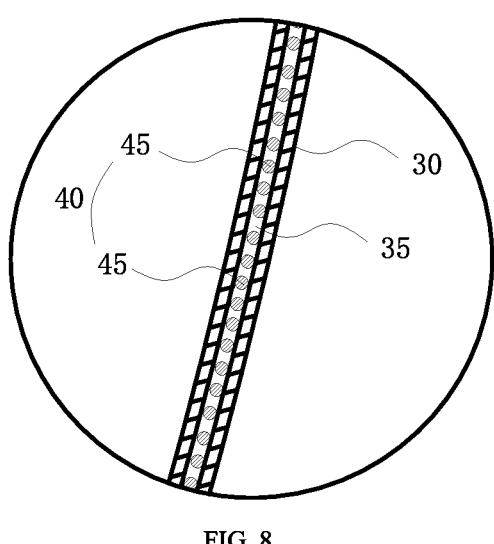
FIG. 8

COVERED STENT

FIELD

The embodiments relate to the field of interventional medical instruments, and in particular, to a covered stent.

BACKGROUND

In the past ten years, the use of aortic covered stents for endovascular isolation of diseased blood vessels has been widely used in aneurysms, arterial dissections and other lesions of thoracic and abdominal aortas. It provides a definite curative effect, only creates a small wound, provides quick recovery, and results in fewer complications, thus becoming a first-line therapy. During the procedure, under fluoroscopy, a covered stent is delivered to a lesion location through a corresponding delivery system. The covered stent isolates a blood flow from the lesion location and eliminates the influence of the blood pressure on the lesion location to achieve a healing purpose. Since the human vascular structure is complicated, and includes many arterial branch vessels, using a covered stent would affect the blood supply to the arterial branch vessels for special lesion parts such as the aortic arch, the celiac artery trunk, the bilateral renal arteries or the superior mesenteric artery. In view of this situation, it is necessary to form an expected hole on the covered stent, and to establish a guide wire track from the hole of the covered stent to the arterial branch vessel. This requires that the edge of the hole has a good imaging means and a good supporting performance to ensure that a guide wire can pass through the hole smoothly to establish the guide wire track.

However, the existing covered stent is generally provided with 4 imaging markers or points at the edge of the hole, i.e., one for each of the top, bottom, left and right parts. Because there is less distribution of the imaging points, it is difficult to accurately determine the position of the edge of the hole during the establishment of the guide wire track. As a result, it is difficult for the guide wire to pass through the hole smoothly, and this prolongs the procedure time.

SUMMARY

The present invention is directed to providing a covered stent that overcomes the drawbacks in the presently available covered stents.

The technical solution used by the embodiments of the present invention to solve the technical problems is as follows.

Provided is a covered stent, including a hollow tubular main body, and a window provided on a side wall of the tubular main body. An elastic supporting member is provided at a periphery of the window; an imaging member is provided on the elastic supporting member; and at least part of the imaging member is movably connected to the elastic supporting member.

In the covered stent of the embodiment, the imaging member is spirally wound around an outer surface of the elastic supporting member.

In the covered stent of the embodiment, the imaging member includes a plurality of spiral units wound around the elastic supporting member; each spiral unit includes two connected connecting portions; and an included angle between a tangent line corresponding to intersections of the connecting portions and the elastic supporting member and a center line of the connecting portions is 75 to 90 degrees.

In the covered stent of the embodiment, the elastic supporting member has an open-loop structure. In a natural state, two end portions of the elastic supporting member partially overlap.

In the covered stent of the embodiment, the overlap part of the two end portions of the elastic supporting member is located in a middle region of the elastic supporting member.

In the covered stent of the embodiment, a wrapping member is wrapped outside the elastic supporting member and the imaging member.

In the covered stent of the present invention, a separator is provided between the elastic supporting member and the imaging member.

In the covered stent of the embodiment, a mounting slot is formed in the elastic supporting member; the imaging member is movably connected into the mounting slot; or, the imaging member includes a plurality of ring-like imaging units, and the imaging units movably surround the elastic supporting member.

In the covered stent of the embodiment, the imaging member includes at least one imaging section; the imaging section includes a movable portion movably connected to the elastic supporting member, and a fixed portion fixedly connected to the elastic supporting member; and the fixed portion is located outside a proximal end region and a distal end region of the elastic supporting member.

In the covered stent of the embodiment, the developing member includes two imaging sections; the two imaging sections are symmetrical about a connecting line of a proximal end and a distal end of the elastic supporting member; the imaging sections are spirally wound around the outer surface of the elastic supporting member; and the imaging sections are entirely located outside the proximal end region and the distal end region of the elastic supporting member.

Provided is another covered stent, including a hollow tubular main body, and a window provided on a side wall of the tubular main body. An elastic supporting member is provided at a periphery of the window; an imaging member is provided on the elastic supporting member; the imaging member includes a fixed portion fixedly connected to the elastic supporting member; and the fixed portion is located outside a proximal end region and a distal end region of the elastic supporting member.

In the covered stent of this embodiment, the imaging member includes at least one developing section; the imaging section is spirally wound around an outer surface of the elastic supporting member; and the imaging section includes the fixed portion, and a movable portion movably connected to the elastic supporting member.

In the covered stent of this embodiment, the fixed portion is located at two ends of the imaging section.

In the covered stent of this embodiment, the imaging section is entirely located outside the proximal end region and the distal end region of the elastic supporting member.

In the covered stent of the present invention, the imaging section includes a plurality of spiral units wound around the elastic supporting member; each spiral unit includes two connected connecting portions; and an included angle between a tangent line corresponding to intersections of the connecting portions and the elastic supporting member and a center line of the connecting portions is 75 to 90 degrees.

In the covered stent of the embodiment, the elastic supporting member has an open-loop structure. In a natural state, two end portions of the elastic supporting member partially overlap.

In the covered stent of the embodiment, the overlapping part of the two end portions of the elastic supporting member is located in a middle region of the elastic supporting member.

In the covered stent of the embodiment, a wrapping member is wrapped outside the elastic supporting member and the imaging member.

In the covered stent of the embodiment, a separator is provided between the elastic supporting member and the imaging member.

According to the above, implementation of the covered stent of the present invention has the following effects: since the imaging member and the elastic supporting member are located at the periphery of the window, the imaging member and the elastic supporting member can enable the periphery of the window to simultaneously have a good imaging performance and a good supporting performance. Furthermore, since the imaging member and the elastic supporting member are movably connected, in case of a bending deformation, the imaging member and the elastic supporting member may move relative to each other, and the imaging member moves away from a region of the elastic supporting member having a greater deformation to avoid obvious bending of the imaging member.

BRIEF DESCRIPTION OF THE DRAWINGS

FIG. 5a and FIG. 5b are comparison diagrams of the spiral unit of the imaging member shown in FIG. 2;

FIG. 6 is a schematic diagram illustrating that the elastic supporting member shown in FIG. 2 has a closed-loop structure;

FIG. 7a is a schematic diagram illustrating that end portions of the elastic supporting member shown in FIG. 2 are provided with spherical portions;

FIG. 7b is a schematic diagram illustrating that end portions of the elastic supporting member shown in FIG. 2 are provided with ring-like structures;

FIG. 8 is a schematic diagram of a developing member and an elastic supporting member at a periphery of a window of a covered stent provided by Embodiment II;

DETAILED DESCRIPTION OF THE EMBODIMENTS

In order to make the foregoing objectives, features and advantages of the present invention clearer and understandable, the specific implementation modes of the present invention are described below in detail with reference to the accompanying drawings. Many specific details are described in the following descriptions to facilitate full understanding of the present invention. However, the present invention can be implemented in a variety of other ways than those described herein, and those skilled in the art can make similar improvements without departing from the connotation of the present invention. Therefore, the present invention is not limited by specific implementations disclosed below.

It should be noted that when an element is referred to as being "fixed" or "provided" to another element, it can be directly on the other element or an intermediate element may also exist. When one element is considered to be "connected" to another element, it can be directly connected to the other element or an intermediate element may be present at the same time. The terms "perpendicular", "horizontal", "left", "right" and similar expressions used herein are for illustrative purposes only, and are not meant to be the only implementation modes.

Unless otherwise defined, all technical and scientific terms used herein are the same as meanings of general understandings of those skilled in the art of the present invention. The terms used in the description of the present invention herein are merely to describe the specific implementation modes, not intended to limit the present invention. The term "and/or" used herein includes any and all combinations of one or more related listed items.

In the interventional medical field, it is generally defined that an end of a covered stent close to the heart after being released is a proximal end, and an end away from the heart is a distal end.

Figure 1:
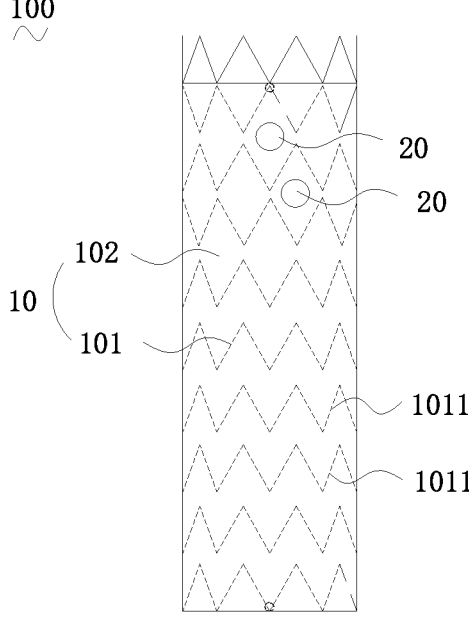
FIG. 1 is a schematic diagram of a covered stent provided by Embodiment I.

Referring to FIG. 1, Embodiment I of the present invention provides a covered stent 100, including a hollow tubular main body 10, and a window 20 provided on a side wall of the tubular main body 10. A tube cavity of the tubular main body 10 is formed into a blood flow channel. The tubular main body 10 includes a bare stent 101, and a cover film 102 connected to the bare stent 101. The bare stent 101 is made of a highly biocompatible material, such as nickel-titanium and stainless steel. The bare stent 101 includes a plurality of turns of waveform ringlike objects 1011. The plurality of turns of waveform ringlike objects 1011 are sequentially arranged at intervals from the proximal end to the distal end, or are connected into a grid structure. The cover film 102 is made of a highly biocompatible macromolecular material, such as PTFE, FEP, PET, and the like.

Figure 2:
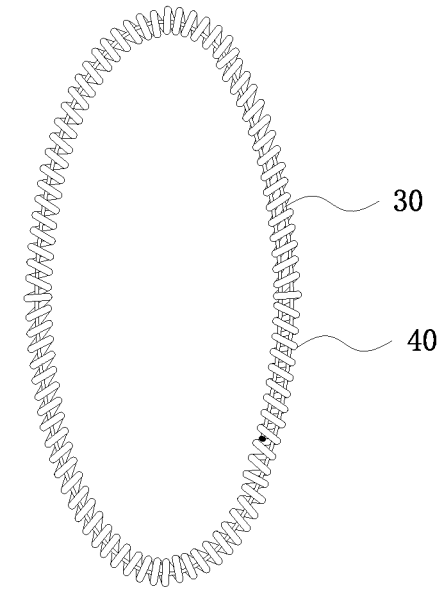
FIG. 2 is a schematic diagram of an imaging member and an elastic supporting member at a periphery of a window of the covered stent shown in FIG. 1.

Referring to FIG. 1 and FIG. 2, a periphery of the window 20 is provided with an elastic supporting member 30. An imaging member 40 is provided on the elastic supporting member 30, and is movably connected to the elastic supporting member 30. The covered stent 100 may radially extrude the elastic supporting member 30 when compressed into a sheath, and at this time, the elastic supporting member 30 may have an obvious bending deformation, particularly in its proximal end and distal end regions. Since the imaging member 40 and the elastic supporting member 30 are movably connected, in case of a bending deformation, the imaging member 40 and the elastic supporting member 30 may move relative to each other, and the imaging member 40 moves away from a region of the elastic supporting member 30 having a greater deformation to avoid obvious bending of the imaging member 40. Furthermore, since the imaging member 40 and the elastic supporting member 30 are located at the periphery of the window 20, the imaging member 40 and the elastic supporting member 30 enable the periphery of the window 20 to simultaneously have a good imaging performance and a good supporting performance.

The elastic supporting member 30 is made of a material with larger elastic modulus, such as nickel-titanium alloy, to enable the periphery of the window 20 to have good compression and resilience characteristics. The imaging member 40 is made of a highly biocompatible material having an X-ray-proof characteristic, such as gold, tantalum niobium alloy and platinum-iridium alloy, to enable the periphery of the window 20 to have a good imaging performance. However, this material has a smaller elastic modulus, so that the elastic modulus of the imaging member 40 is less than the elastic modulus of the elastic supporting member 30. The elastic modulus of the imaging member 40 is relatively small, so that in case of a deformation, the imaging member 40 has a plastic deformation that can easily restrain the resilience of the elastic supporting member 30 connected thereto. As a result, the window 20 cannot be opened completely, and the opening size of the window 20 is reduced, thereby affecting the establishment of a guide wire track. The imaging member 40 and the elastic supporting member 30 of the present invention are movably connected, so that in case of a deformation, the imaging member 40 may move along the elastic supporting member 30, and move to the part of the elastic supporting member 30 having a lesser deformation to avoid the plastic deformation in the imaging member 40.

Figure 3:
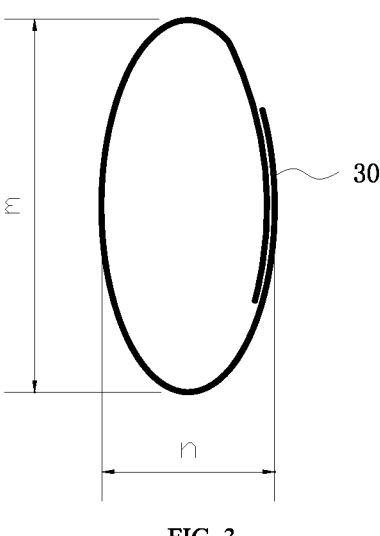
FIG. 3 is a schematic diagram illustrating that the elastic supporting member shown in FIG. 2 has an open-loop structure.

Referring to FIG. 3, the elastic supporting member 30 has an open-loop structure. In a natural state, two end portions of the elastic supporting member 30 will partially overlap. At this time, the elastic supporting member 30 covers the entire periphery of the window 20 to completely support the shape of the window 20. Because the elastic supporting member 30 has an open-loop structure, in case of an elastic deformation, the two end portions of the elastic supporting member 30 may move relative to each other to facilitate radial compression and resilient deformation of the elastic supporting member 30.

The proximal end and distal end regions of the elastic supporting member 30 greatly deform, so that if the overlapping parts of the two end portions of the elastic supporting member 30 are located in or close to the proximal end and distal end regions of the elastic supporting member 30, in the case of a deformation, the end portions of the elastic supporting member 30 easily extend out from a spiral clearance of a imaging section 44 to affect their later relative movement. Therefore, in order to avoid the influence of the bending deformation on the relative movement between the two end portions, the overlapping part of the two end portions of the elastic supporting member 30 is located in a middle region of the elastic supporting member 30. It should be noted that the "middle region of the elastic supporting member" refers to a region covered by points on the elastic supporting member 30 where perpendicular distances from the proximal end to the distal end of the elastic supporting member are greater than or equal to 2 mm.

The elastic supporting member 30 is elliptical, having a long axis m which is approximately parallel to a generatrix direction of the covered stent 100, and a short axis n which is approximately perpendicular to the generatrix direction of the covered stent 100. Since the short axis n has a relatively small size, when the covered stent 100 is compressed into a sheath, the elastic supporting member 30 is easily compressed radially, and a resilience force generated in the sheath is relatively low, which is also favorable for reducing the resistance of release. In the present embodiment, a ratio of the long axis m to the short axis n of the elastic supporting member 30 is preferably 3/2≤m/n≤3 to facilitate the radial compression and resilient deformation of the elastic supporting member 30.

Referring to FIG. 2 again, the imaging member 40 is spirally wound around the entire outer surface of the elastic supporting member 30; an inner diameter of a spiral structure encircled by the imaging member 40 is greater than an outer diameter of the elastic supporting member 30, so that the imaging member 40 can movably surround the outside of the elastic supporting member 30; and when the elastic supporting member 30 has an elastic deformation, the two end portions of the elastic supporting member 30 are always located within the spiral structure encircled by the imaging member 40. A diameter of an inscribed circle of a cross section of an imaging wire of the imaging member 40 is greater than or equal to 0.1 mm, and preferably between 0.1 mm to 0.5 mm, to ensure that the imaging member 40 has a good imaging performance. It can be understood that, in other embodiments, the imaging member 40 may also be wound around only a part of the outer surface of the elastic supporting member 30.

Figures 4A, 4B:
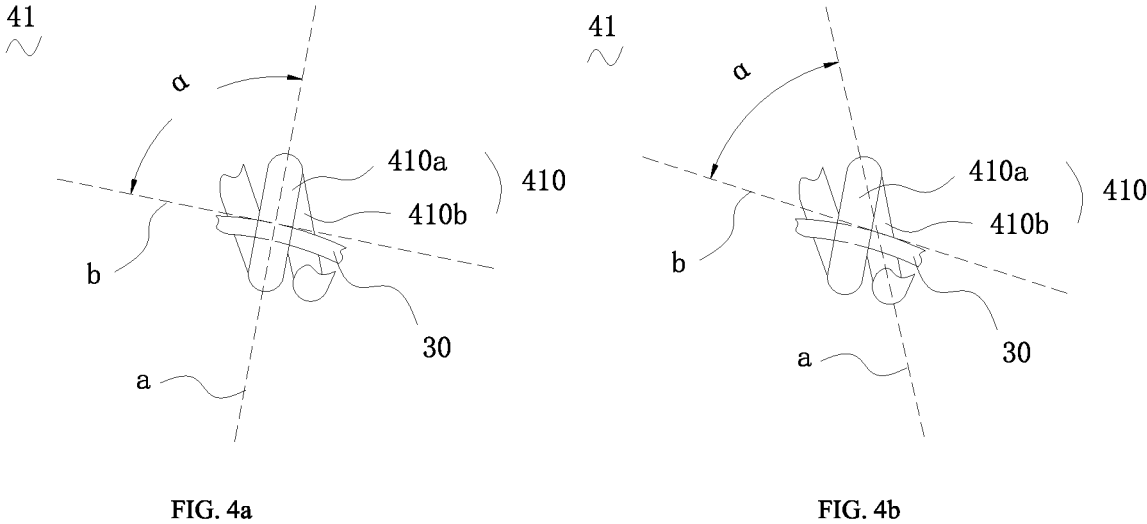
FIG. 4a and FIG. 4b are schematic diagrams of a spiral unit of the imaging member shown in FIG. 2.

Referring to FIG. 4a and FIG. 4b, the imaging member 40 includes a plurality of spiral units 41 wound around the elastic supporting member 30. Each spiral unit 41 includes two connected connecting portions 410: a first connecting portion 410a and a second connecting portion 410b. An included angle between a tangent line b corresponding to intersections of the connecting portions 410 and the elastic supporting member 30 and a center line a of the connecting portions 410 is a, 75°≤a≤90°. Referring to FIG. 5a and FIG. 5b, if the included angle α between the tangent line b corresponding to the intersections of the connecting portions 410 and the elastic supporting member 30 and the center line a of the connecting portions 410 is smaller, when the elastic supporting member 30 has a bending deformation, the connecting portions 410 will easily have the same bending deformation together with the elastic supporting member 30, thereby affecting the relative movement between the imaging member 40 and the elastic supporting member 30. Furthermore, the elastic modulus of the imaging member 40 is relatively small, so that in case of a deformation, the imaging member 40 will easily have a plastic deformation, thereby affecting the resilience of the elastic supporting member 30. Therefore, in the present invention, the above-mentioned included angle α is set within a range between 75 degrees and 90 degrees, so that the relative movement between the imaging member 40 and the elastic supporting member 30 cannot be affected by the bending deformation, and the plastic deformation of the imaging member 40 is avoided.

It can be understood that the present invention does not define the specific structure of the elastic supporting member 30. In other embodiments, the elastic supporting member 30 may also be of a closed-loop structure or a circular-ring-shaped structure, as long as it is ensured that the elastic supporting member 30 is movably connected to the imaging member 40. For example, in the embodiment shown in FIG. 6, the elastic supporting member 30 has an elliptical closed-loop structure. Or, in the embodiment shown in FIG. 7a and FIG. 7b, the elastic supporting member 30 has an elliptical open-loop structure. In a natural state, the two end portions of the elastic supporting member 30 at least partially overlap. The two end portions of the elastic supporting member 30 are provided with spherical portions 31 or ring-like structures 32. The imaging member 40 is spirally wound around the outer surface of the elastic supporting member 30. The radial sizes of the spherical portion 31 and the ring-like structure 32 are greater than a clearance between two adjacent first connecting portions 410a (or second connecting portions 410b) to avoid the end portions of the elastic supporting member 30 from going through the clearances of the developing member 40 during relative movement of the imaging member 40 and the elastic supporting member 30, and to ensure that the two end portions of the elastic supporting member 30 are always located in a spiral structure encircled by the imaging member 40.

The elastic supporting member 30 and the imaging member 40 are both made of metal materials, so that a potential difference exists between them. If they are in direct contact with blood, electrochemical corrosion and chemical corrosion can easily occur, which can cause the elastic supporting member 30 and the imaging member 40 to break, and the broken elastic supporting member 30 or imaging member 40 can enter in vivo circulation to cause serious injury to a patient. Therefore, during assembly, the elastic supporting member 30 connected with the imaging member 40 can be placed into the hollow wrapping member (not shown), and then the wrapping member is fixed at the periphery of the window 20.

The wrapping member has a ring-like structure, and is made of a highly biocompatible macromolecular material, preferably blood-proof PTFE, ePTFE, and the like. The elastic supporting member 30 is movably arranged in the wrapping member, and the wrapping member does not affect the movable connection between the elastic supporting member 30 and the imaging member 40. The wrapping member is wrapped outside the elastic supporting member 30 and the imaging member 40, so that even if the elastic supporting member 30 or the imaging member 40 is broken, the broken structure would not enter a human body to injure the patient.

During actual manufacturing, after the window 20 is formed in the cover film 102, the elastic supporting member 30 connected with the imaging member 40 is placed at the periphery of the window 20, the cover film 102 at the periphery of the window 20 is then folded towards a side of the elastic supporting member 30 to wrap the elastic supporting member 30 inside; and finally, the cover film 102 on the inner and outer sides of the elastic supporting member 30 is fixedly connected. That is, the wrapping member of the present embodiment is formed by folding the cover film 102 at the periphery of the window 20. It can be understood that the present embodiment does not limit the specific structure of the wrapping member, as long as it is wrapped outside the elastic supporting member 30 and the imaging member 40 and does not affect their movable connection. For example, in other embodiments, the wrapping member and the cover film 102 can be independent components. The wrapping member is fixed at the periphery of the window 20 via suture.

Further, the imaging member 40 is movably wound on the elastic supporting member 30, so that when they move relative to each other, a friction force between the imaging member 40 and the elastic supporting member 30 can easily cause the elastic supporting member 30 or the imaging member 40 to break. Therefore, a separator (not shown) is provided between the elastic supporting member 30 and the imaging member 40 of the present invention. The separator is made of a highly biocompatible material, such as PTFE, FEP, PET, and the like. The elastic supporting member 30 and the imaging member 40 are separated through the separator, so that friction generated by their direct contact can be avoided, and electrochemical corrosion and chemical corrosion can also be avoided.

In the present embodiment, the separator is wrapped around the entire outer surface of the elastic supporting member 30 via suturing or thermal treatment, or other techniques, and the imaging member 40 movably surrounds the outside of the separator. It can be understood that, in the present embodiment, the position of the separator on the elastic supporting member 30 is not defined. For example, in other embodiments, the separator is only wrapped outside the two end portions of the elastic supporting member 30, and the elastic supporting member 30 has an open-loop structure, because the relative friction between the two end portions is greater, so that wrapping the separator outside the two end portions of the elastic supporting member 30 would effectively prevent the two end portions of the elastic supporting member 30 from being broken.

Referring to FIG. 8, the preferred embodiment II of the present invention provides a covered stent, and differs from Embodiment I in that a mounting slot 35 is formed in the elastic supporting member 30, and the imaging member 40 is movably connected into the mounting slot 35.

The imaging member 40 includes a plurality of spherical first imaging units 45, and the first imaging units 45 may roll in the mounting slot 35. In case of a bending deformation, the imaging member 40 and the elastic supporting member 30 may move relative to each other, and the imaging member 40 moves away from a region of the elastic supporting member 30 having a great deformation to avoid the influence of the imaging member 40 on extrusion and resilient deformation of the elastic supporting member 30.

Figure 9:
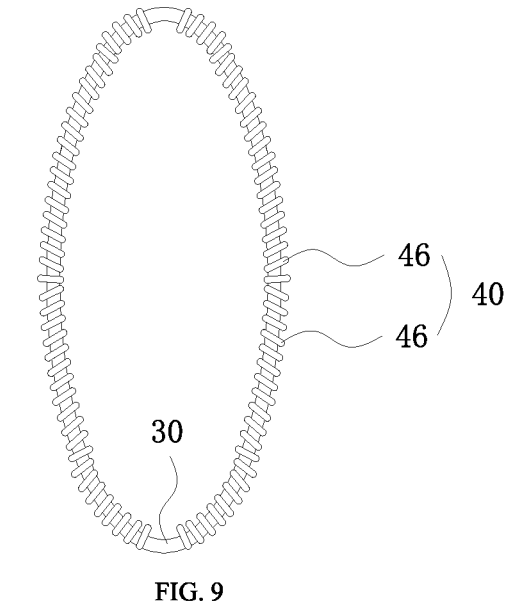
FIG. 9 is a schematic diagram of an imaging member and an elastic supporting member at a periphery of a window of a covered stent provided by Embodiment III.

Referring to FIG. 9, the preferred embodiment III of the present invention provides a covered stent, and differs from Embodiment I in that the imaging member 40 includes a plurality of ring-like second imaging units 46, and each second imaging unit 46 movably surrounds the outside of the elastic supporting member 30. In case of a bending deformation, the second imaging units 46 may move away from a region of the elastic supporting member 30 having a great deformation to avoid the influence of the imaging member 40 on extrusion and resilient deformation of the elastic supporting member 30.

Figure 10:
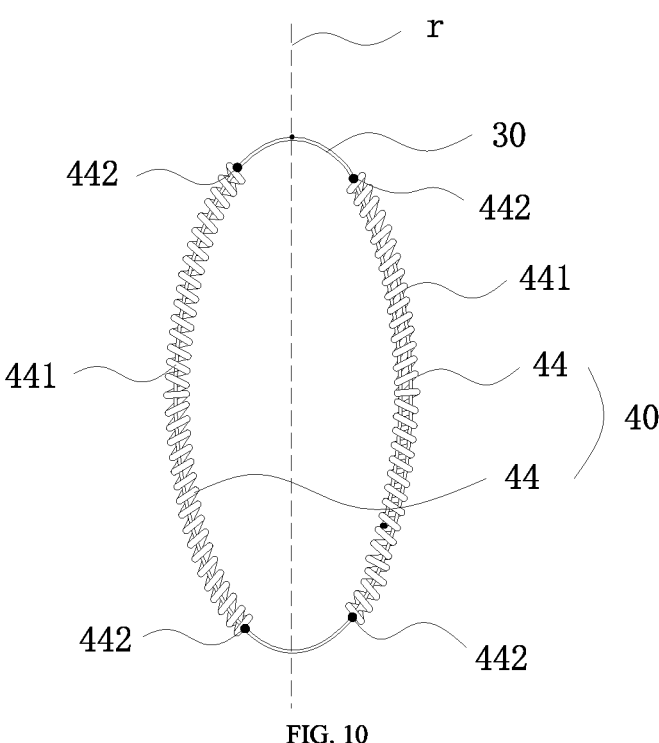
FIG. 10 is a schematic diagram of an imaging member and an elastic supporting member at a periphery of a window of a covered stent provided by Embodiment IV.

Referring to FIG. 10, the preferred embodiment IV of the present invention provides a covered stent, and differs from Embodiment I in that the imaging member 40 includes two imaging sections 44 spaced apart from each other; the two imaging sections 44 are symmetrical about a connecting line r of the proximal end and the distal end of the elastic supporting member 30, and are located outside a proximal end region and a distal end region of the elastic supporting member 30. It should be noted that the "proximal end region and the distal end region of the elastic supporting member 30" refers to a region covered by points on the elastic supporting member 30 where perpendicular distances from the proximal end to the distal end of the elastic supporting member are less than or equal to 0.5 mm.

The imaging sections 44 are spirally wound around the outer surface of the elastic supporting member 30. The imaging sections 44 include movable portions 441 movably connected to the elastic supporting member 30, and fixed portions 442 fixedly connected to the elastic supporting member 30; and the fixed portions 442 are fixed on the elastic supporting member 30 by bonding, welding or other techniques. The fixed portions 442 are located at two ends of the developing sections 44, and the movable portions 441 are located between the two ends of the developing sections 44.

In case of a deformation, the movable portions 441 and the elastic supporting member 30 may move relative to each other, and the movable portions 441 move away from a region of the elastic supporting member 30 having a greater deformation to prevent the imaging sections 44 from generating a plastic deformation. The two ends of the imaging sections 44 are fixed, so that even if the movable portions 441 and the elastic supporting member 30 move relative to each other, the positions of all the imaging sections 44 on the elastic supporting member 30 are not affected. That is, the positions of all the imaging sections 44 on the elastic supporting member 30 are fixed, so that the window 20 can be properly imaged and located. Furthermore, in the present embodiment, all the imaging sections 44 are located outside the proximal end region and the distal end region of the elastic supporting member 30, so that all the imaging sections 44 may be kept away from the region of the elastic supporting member 30 having the greater deformation so as to further prevent the imaging sections 44 from generating the plastic deformation.

It can be understood that the present embodiment does not define the specific quantity and positions of the imaging sections 44. There may be one or a plurality of imaging sections 44. The imaging sections 44 may also be located in the proximal end region and the distal end region of the elastic supporting member 30, as long as the fixed portions 442 of the imaging sections 44 are located outside the proximal end region and the distal end region of the elastic supporting member 30.

Figure 11:
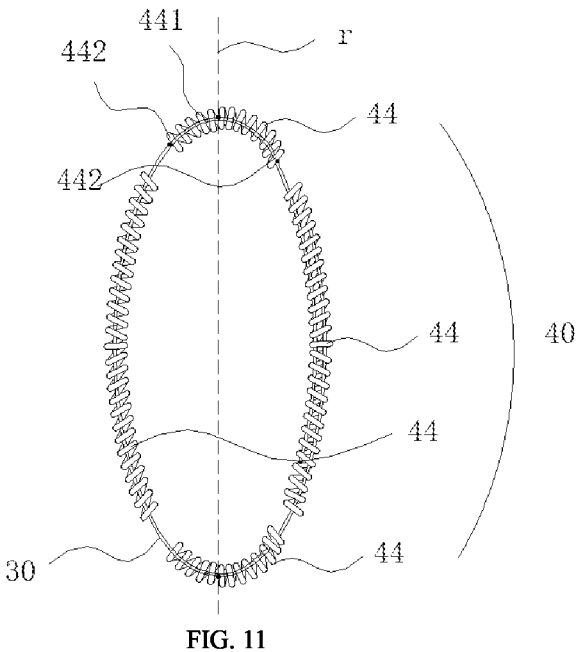
FIG. 11 is a schematic diagram of an imaging member and an elastic supporting member at a periphery of a window of a covered stent provided by Embodiment V.
Figure 12:
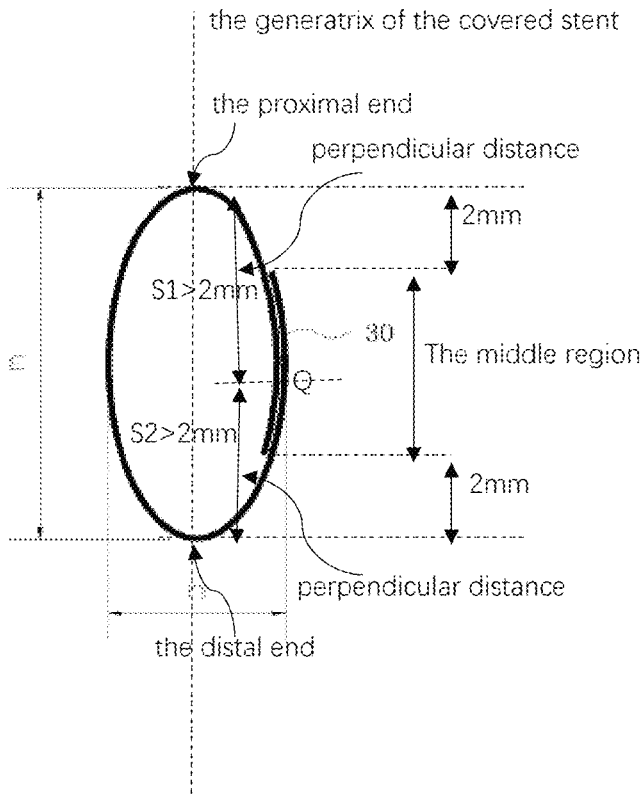
FIG. 12 is a schematic diagram of the elastic supporting member shown in FIG. 3 and labeled to show the middle region of the elastic supporting member.

Referring to FIG. 11, the preferred embodiment V of the present invention provides a covered stent, and differs from Embodiment IV in that the imaging sections 44 may also be located in the proximal end region and the distal end region of the elastic supporting member 30, as long as the fixed portions 442 of the imaging sections 44 are located outside the proximal end region and the distal end region of the elastic supporting member 30. For example, the imaging member 40 includes four imaging sections 44 provided spaced apart from each other; the imaging sections 44 are spirally wound around the outer surface of the elastic supporting member 30; the imaging sections 44 include fixed portions 442, and movable portions 441 movably connected to the elastic supporting member 30; the fixed portions 442 are located at two ends of the imaging sections 44, and are located outside the proximal end region and the distal end region of the elastic supporting member 30; and the movable portions 441 are located between the two ends of the imaging sections 44.

The technical features of the embodiments described above can be arbitrarily combined. In order to simplify the description, all possible combinations of the technical features in the above embodiments have not been described. However, the combinations of these technical features should be considered as being within the scope described in this description as long as there is no contradiction among them.

The above-mentioned embodiments only express several implementation modes of the present disclosure, and their descriptions are more specific and detailed, but they cannot be understood as limiting the patent scope of the present disclosure. It should be noted that those of ordinary skill in the art can further make various transformations and improvements without departing from the scope of the present disclosure, and these transformations and improvements all fall within the protection scope of the present disclosure. Therefore, the protection scope of the patent of the present invention shall be subject to the appended claims.

What is claimed is:

1. A covered stent, comprising a hollow tubular main body, and a window provided on a side wall of the tubular main body, wherein an elastic supporting member is provided at a periphery of the window; an imaging member is provided on the elastic supporting member; and at least part of the imaging member is movably connected to the elastic supporting member;

wherein the elastic supporting member has an open-loop structure, and in a natural state, two end portions of the elastic supporting member partially overlap; and wherein the two end portions of the elastic supporting member may move relative to each other;

wherein the imaging member has a long axis m which is approximately parallel to a generatrix direction of the covered stent, and a short axis n which is approximately perpendicular to the generatrix direction of the covered stent; and wherein the covered stent includes a compression state and a natural state, the covered stent can transition between the compression state and the natural state, and the overlapping portions of the two ends of the elastic supporting member are located in a middle region of the elastic supporting member, wherein the middle region is covered by points on the elastic supporting member, and a first perpendicular distance from any of the points in the middle region of the elastic supporting member to the proximal end of the elastic supporting member and a second perpendicular distance from any of the points in the middle region of the elastic supporting member to the distal end of the elastic supporting member are greater than or equal to 2 mm, so that the proximal end and the distal end of the elastic supporting member are always located in the imaging member in the compression state and the natural state, and during the process of transitioning between the compression state to the natural state.

2. The covered stent according to claim 1, wherein a ratio of the long axis m to the short axis n of the elastic supporting member is $3/2 \leq m/n \leq 3$.

3. The covered stent according to claim 1, wherein the imaging member and the elastic supporting member respectively have an elastic modulus, and the elastic modulus of the imaging member is less than the elastic modulus of the elastic supporting member.

4. The covered stent according to claim 1, wherein the imaging member is spirally wound around an outer surface of the elastic supporting member.

5. The covered stent according to claim 4, wherein the imaging member comprises a plurality of spiral units wound around the elastic supporting member; each spiral unit comprises two connected connecting portions; and an included angle between a tangent line corresponding to intersections of the connecting portions and the elastic supporting member and a center line of the connecting portions is 75 to 90 degrees.

6. The covered stent according to claim 5, wherein the two end portions of the elastic supporting member are provided with spherical portions or ring-like structures, and radial sizes of the spherical portion and the ring-like structure are greater than a clearance between the two adjacent connecting portions.

7. The covered stent according to claim 1, wherein a mounting slot is formed in the elastic supporting member; the imaging member is movably connected into the mounting slot; or, the imaging member comprises a plurality of ring-like imaging units, and the imaging units movably surround the elastic supporting member.

8. The covered stent according to claim 1, wherein the imaging member comprises at least one imaging section; the imaging section comprises a movable portion movably connected to the elastic supporting member, and a fixed portion fixedly connected to the elastic supporting member; 5 and the fixed portion is located outside a proximal end region and a distal end region of the elastic supporting member.

9. The covered stent according to claim 8, wherein the imaging member comprises two imaging sections; the two 10 imaging sections are symmetrical about a connecting line of a proximal end and a distal end of the elastic supporting member; the imaging sections are spirally wound around the outer surface of the elastic supporting member; and all the imaging sections are located outside the proximal end region 15 and the distal end region of the elastic supporting member.

* * * * *